(12) United States Patent
Kim et al.

(10) Patent No.: US 9,700,380 B2
(45) Date of Patent: Jul. 11, 2017

(54) METHOD FOR PROVIDING GUIDE INFORMATION OF OPERATION USING SURGICAL GUIDE

(71) Applicant: DIO Corporation, Busan (KR)

(72) Inventors: Jin Chul Kim, Yangsan-si (KR); Jin Baek Kim, Busan (KR)

(73) Assignee: DIO CORPORATION, Busan (KR)

( * ) Notice: Subject to any disclaimer, the term of this patent is extended or adjusted under 35 U.S.C. 154(b) by 0 days.

(21) Appl. No.: 15/081,356

(22) Filed: Mar. 25, 2016

(65) Prior Publication Data

US 2016/0287336 A1 Oct. 6, 2016

(30) Foreign Application Priority Data

Apr. 1, 2015 (KR) ........................ 10-2015-0045924

(51) Int. Cl.

| | |
|---|---|
| G06T 1/00 | (2006.01) |
| A61B 34/10 | (2016.01) |
| A61C 1/08 | (2006.01) |
| G06K 9/62 | (2006.01) |
| G06T 7/00 | (2017.01) |
| A61B 6/03 | (2006.01) |
| A61B 6/14 | (2006.01) |
| A61B 6/00 | (2006.01) |
| A61B 34/00 | (2016.01) |

(52) U.S. Cl.
CPC ............. *A61B 34/10* (2016.02); *A61B 6/032* (2013.01); *A61B 6/14* (2013.01); *A61B 6/5247* (2013.01); *A61C 1/084* (2013.01); *G06K 9/6201* (2013.01); *G06K 9/6267* (2013.01); *G06T 7/0012* (2013.01); *A61B 6/505* (2013.01); *A61B 6/5217* (2013.01); *A61B 2034/108* (2016.02); *A61B 2034/252* (2016.02); *G06T 2207/10012* (2013.01); *G06T 2207/10081* (2013.01); *G06T 2207/30036* (2013.01)

(58) Field of Classification Search
None
See application file for complete search history.

(56) References Cited

U.S. PATENT DOCUMENTS

| | | | | |
|---|---|---|---|---|
| 2009/0092948 | A1* | 4/2009 | Gantes | A61C 1/084 433/215 |
| 2010/0105011 | A1* | 4/2010 | Karkar | A61C 1/084 433/215 |
| 2015/0073760 | A1* | 3/2015 | Sachidanandam | G06F 3/0482 703/7 |

FOREIGN PATENT DOCUMENTS

| | | | | |
|---|---|---|---|---|
| IT | EP 2044903 | A2 * | 4/2009 | ............. A61C 1/084 |

* cited by examiner

*Primary Examiner* — Delomia L Gilliard
(74) *Attorney, Agent, or Firm* — Paratus Law Group, PLLC

(57) ABSTRACT

A method for providing procedure guide information using a surgical guide for a dental implant, including: causing a computed tomography image and an oral scan image of a patient to acquire a combined three-dimensional image; selecting a fixture corresponding to a preset implant placement position, preparing the surgical guide in which at least one guide hole configured to guide drilling of a hole used to place the fixture is formed, and causing information about the placement of the fixture and information about drilling guidance to be calculated and prepared as information about a procedure report; outputting the procedure report; and delivering the output procedure report according to information about delivery of the surgical guide.

4 Claims, 5 Drawing Sheets

METHOD FOR PROVIDING GUIDE INFORMATION OF OPERATION USING SURGICAL GUIDE

CROSS-REFERENCE TO RELATED APPLICATION

This application claims priority to Korean Patent Application No. 10-2015-0045924, filed on Apr. 1, 2015, the disclosure of which is incorporated herein by reference in its entirety.

BACKGROUND

1. Field of the Invention

The present invention relates to a method for providing procedure guide information for a dental implant using a surgical guide for a dental implant and, more particularly, to a method for providing procedure guide information using a surgical guide for a dental implant such that convenience of a procedure using the surgical guide is improved.

2. Discussion of Related Art

Implants generally refer to replacement materials capable of replacing damaged human tissue, and particularly artificial teeth in dentistry. An implant procedure is a procedure for placing a fixture made of, for instance, titanium, etc. which is free from a rejection reaction by a human body in an alveolar bone from which a natural tooth has been removed such that the fixture can replace a missing root of the natural tooth and then fixing an abutment and a crown to the fixture to recover a function of the natural tooth.

The implant procedure is made up of a process of drilling a hole in an alveolar bone, a process of placing a fixture in the alveolar bone, and a process of coupling an abutment and a crown to the fixture. Here, the processes of drilling the hole and placing the fixture show great differences between patients. This is because a position, a direction, and a depth of an implant are decided in view of various factors such as conditions of the alveolar bone of a patient, a position of a tooth required for the implant, and so on.

In these processes of drilling the hole and placing the fixture, surgeons with little experience in the procedure as well as experienced surgeons have considerable difficulties in accurately evaluating the depth and direction of the implant.

For this reason, a method of assisting the processes of drilling the hole and placing the fixture using a surgical guide prepared on the basis of a three-dimensional image acquired through computed tomography (CT) and oral scan of an oral cavity of a patient is being used.

Here, the surgical guide is prepared to be able to acquire CT and oral scan images of the inside of the oral cavity of the patient, establish an implant procedure plan from a result of matching the two images, and guide a procedure according to the implant procedure plan.

Then, a hole is drilled in an alveolar bone of the patient on the basis of the prepared surgical guide, and a fixture is selected and placed according to a type of tooth corresponding to a position of the hole. At this time, in the surgical guide, each guide hole rotatably supporting a circumference of a drill bit is formed at a position corresponding to the position of the drilled hole, and a drilling process is performed under guidance of the guide hole.

Here, the drilling process is made up of various steps such as a step of removing gum tissue, a step of setting a position of an alveolar bone, a step of flattening the alveolar bone, a step of forming and expanding an initial hole, a step of forming threads, and so on. In the drilling process, drills having different diameters and shapes in each of the steps and drill assist devices are used. Further, in the surgical guide, the drills and the drill assist devices used in each of the steps may be changed according to a position of the guide hole formed corresponding to the position at which the implant of the patient is placed, a diameter of the drilled hole, and the conditions of the alveolar bone.

Moreover, a fixture having a diameter and a height suitable for the hole drilled under the guidance of the guide hole should be implanted.

Accordingly, there is a problem in that confusion arises for a surgeon when selecting the appropriate drills and the drill assist devices according to each of the steps of the drilling process, the position of the guide hole, and the conditions of the alveolar bone and when placing the fixture matched with the drilled hole, and thus causing a procedure to be delayed.

That is, as each of the drills is selected according to memory or experience of a surgeon, the order of the selected drill is frequently changed by a mistake of the surgeon. For this reason, the diameter or internal threads of the drilled hole are not accurately formed, and osseointegration becomes slow after the fixture is placed. In more serious cases, the fixture becomes twisted after the osseointegration.

SUMMARY OF THE INVENTION

The present invention is directed to a method for providing procedure guide information using a surgical guide for a dental implant such that convenience of a procedure using the surgical guide is improved.

To achieve the above object, a method for providing procedure guide information using a surgical guide for a dental implant according to an aspect of the present invention includes: a first step of causing a computed tomography (CT) image and an oral scan image of an inside of an oral cavity of a patient to be image-matched to acquire a combined three-dimensional image; a second step of selecting a fixture corresponding to a preset implant placement position on the basis of the acquired combined three-dimensional image, preparing the surgical guide in which at least one guide hole configured to guide drilling of a hole used to place the fixture is formed, and causing information about the placement of the fixture corresponding to the guide hole and information about drilling guidance to the hole to be calculated and prepared as information about a procedure report; a third step of outputting the procedure report in which a summary report in which the information about the procedure report is indicated along an image of the surgical guide and a protocol report in which the information about the procedure report is filtered and indicated to be matched to one of the guide holes are included; and a fourth step of delivering the output procedure report according to information about delivery of the surgical guide.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Hereinafter, a method for providing information about a surgical operation using a surgical guide for a dental implant according to an embodiment of the present invention will be described in detail with reference to the accompanying drawings.

Figure 1:
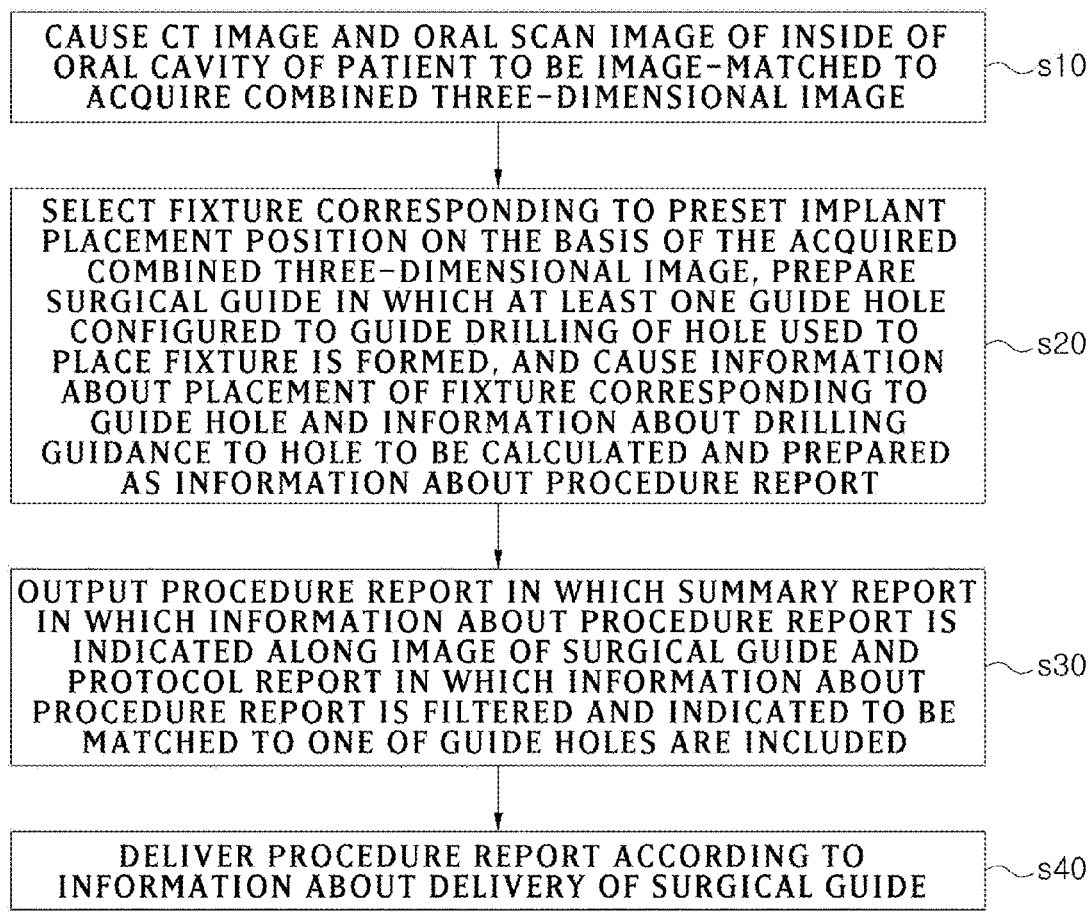
FIG. 1 is a flow chart illustrating a method for providing procedure guide information using a surgical guide for a dental implant according to an embodiment of the present invention.
Figure 2:
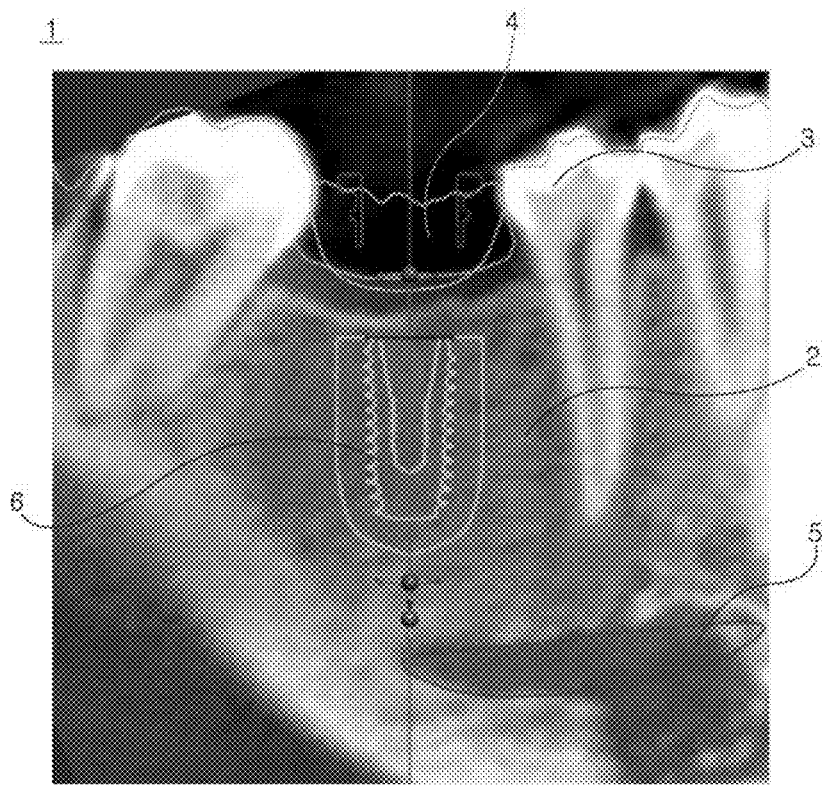
FIG. 2 is a view illustrating a process of selecting a fixture in the method for providing the procedure guide information using the surgical guide for the dental implant according to the embodiment of the present invention.
Figure 3:
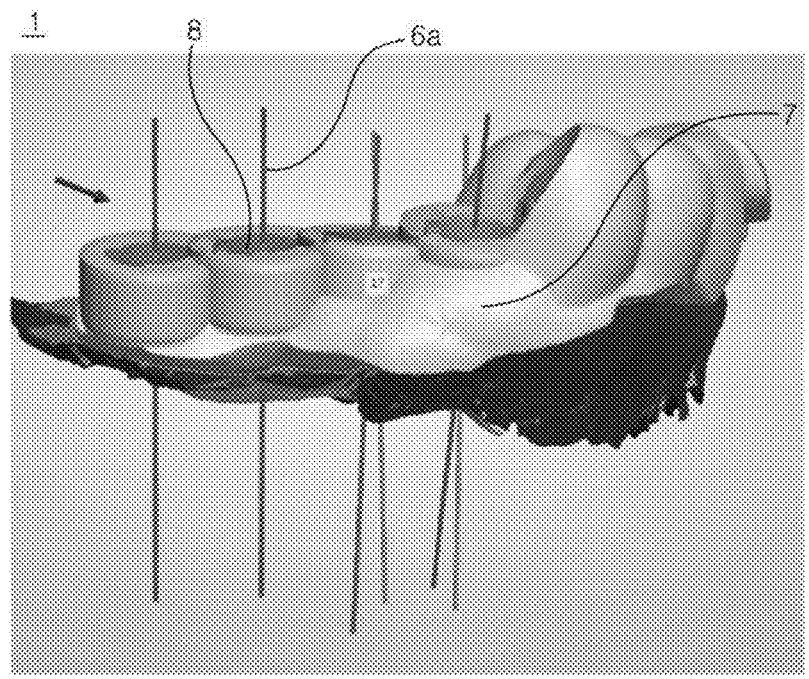
FIG. 3 is a view illustrating a process of setting a direction of a guide hole in the method for providing the procedure guide information using the surgical guide for the dental implant according to the embodiment of the present invention.
Figure 4:
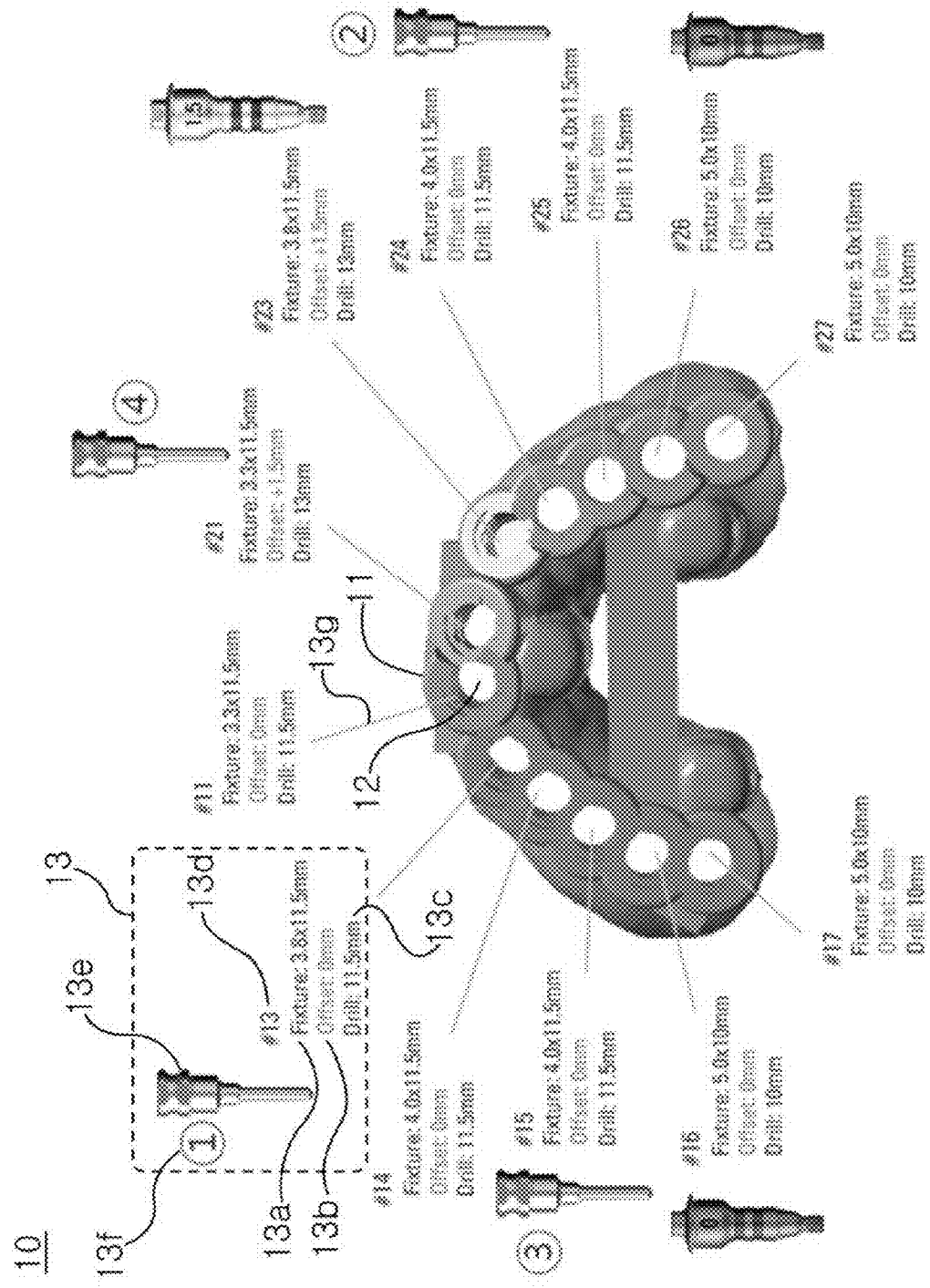
FIG. 4 is a view illustrating a summary report in the method for providing the procedure guide information using the surgical guide for the dental implant according to the embodiment of the present invention.
Figure 5:
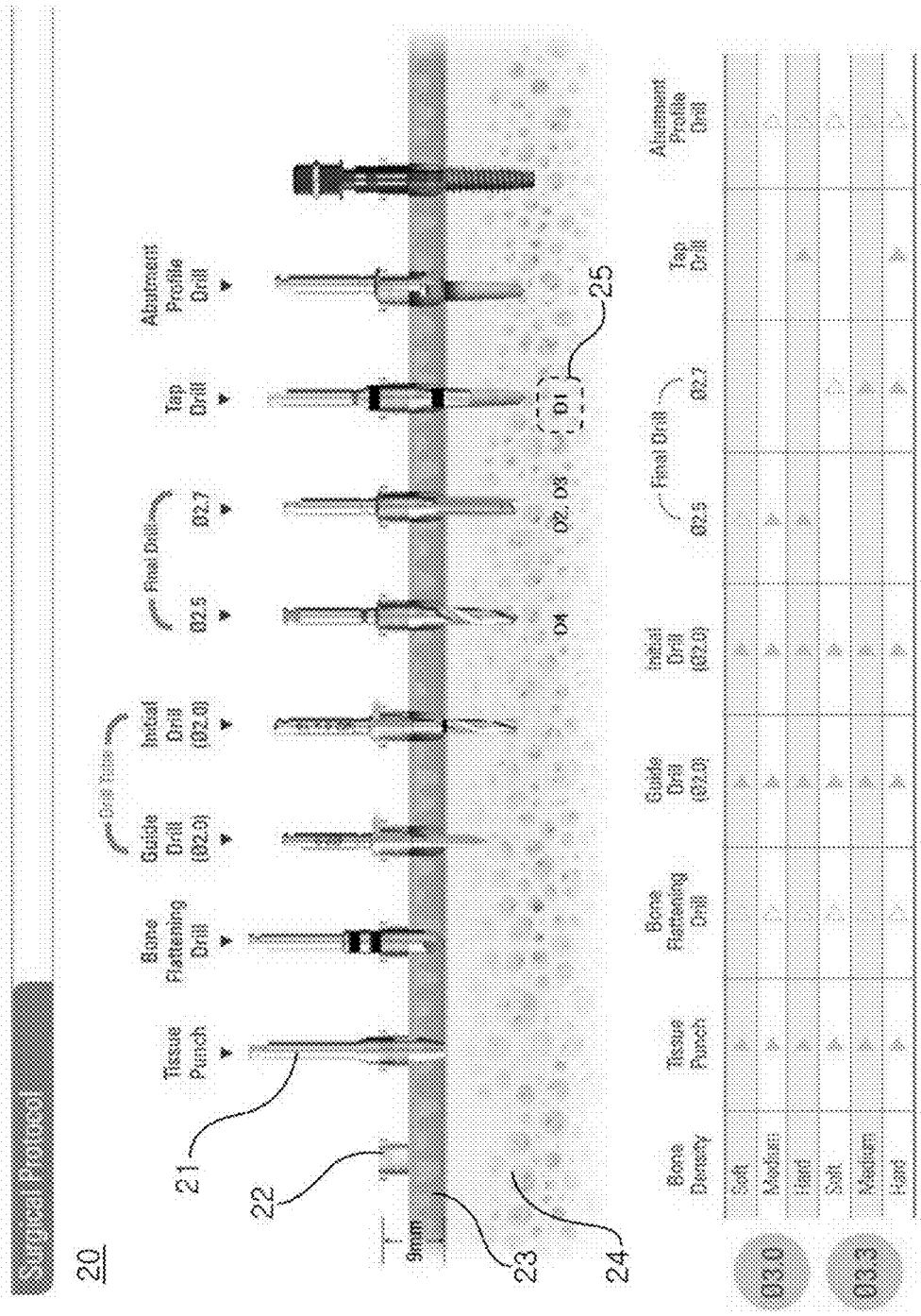
FIG. 5 is a view illustrating a protocol report in the method for providing the procedure guide information using the surgical guide for the dental implant according to the embodiment of the present invention.
Figure 6:
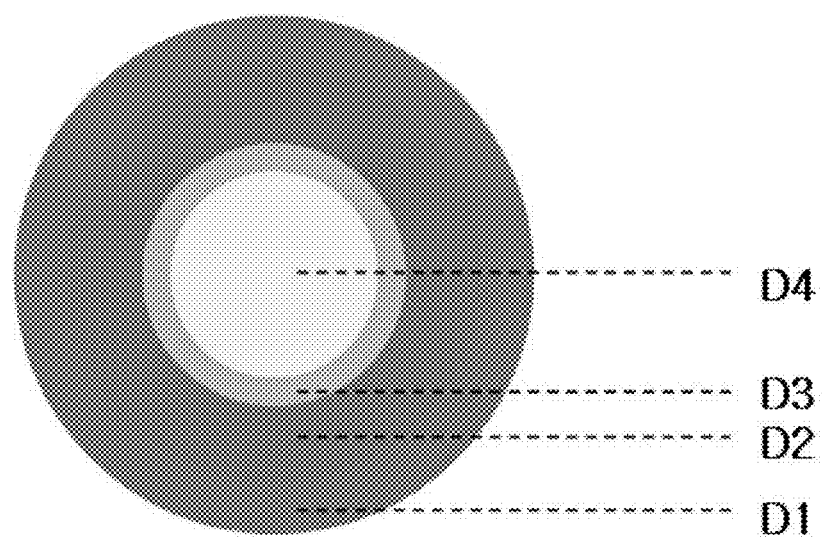
FIG. 6 is a view illustrating an analysis of density of an alveolar bone in the method for providing the procedure guide information using the surgical guide for the dental implant according to the embodiment of the present invention.

FIG. 1 is a flow chart illustrating a method for providing procedure guide information using a surgical guide for a dental implant according to an embodiment of the present invention. FIG. 2 is a view illustrating a process of selecting a fixture in the method for providing the procedure guide information using the surgical guide for the dental implant according to the embodiment of the present invention. FIG. 3 is a view illustrating a process of setting a direction of a guide hole in the method for providing the procedure guide information using the surgical guide for the dental implant according to the embodiment of the present invention. FIG. 4 is a view illustrating a summary report in the method for providing the procedure guide information using the surgical guide for the dental implant according to the embodiment of the present invention. FIG. 5 is a view illustrating a protocol report in the method for providing the procedure guide information using the surgical guide for the dental implant according to the embodiment of the present invention. FIG. 6 is a view illustrating an analysis of density of an alveolar bone in the method for providing the procedure guide information using the surgical guide for the dental implant according to the embodiment of the present invention.

Here, an implant procedure refers to a procedure for replacing a missing tooth with an artificial prosthesis. The prosthesis includes a crown, a fixture corresponding to a dental root, and an abutment connecting the crown and the fixture. The implant procedure may be performed by placing the fixture in a hole formed in an alveolar bone by drilling using an assist mechanism called a surgical guide and then connecting the abutment and the crown to the fixture.

Here, the surgical guide serves to accurately guide a direction, a position, and a depth of the hole formed by the drilling.

As illustrated in FIGS. 1 to 6, a method for providing procedure guide information using a surgical guide for a dental implant according to an embodiment of the present invention is performed by the following processes.

First, a computed tomography (CT) image and an oral scan image of the inside of an oral cavity of a patient are matched, so that a combined three-dimensional image can be acquired (s10). Here, the CT image can provide information about internal tissue of a crown (a dental upper side exposed to the outside of a gum) of each tooth, a dental root (a dental lower side coupled with an alveolar bone in the gum), and the alveolar bone. The oral scan image can provide information about a shape of the crown exposed to the outside and a shape of the gum around the tooth.

At this point, the oral scan image may be acquired by directly scanning the inside of the oral cavity of the patient using, for instance, an oral scanner or by scanning an impression model that is intaglio modeled on the inside of the oral cavity of the patient or a plaster model produced through a relievo of the impression model. Here, a scan image of the impression model may be reversed and acquired as the oral scan image.

The combined three-dimensional image can be acquired by matching the oral scan image and the CT image on the basis of the crown which is a common portion or of a reference marker installed in the oral cavity of the patient.

To improve accuracy of the implant procedure, comprehensive information about dental external and internal tissue is required. That is, an amount of bone, a bone density, and distribution of the alveolar bone, a thickness of the gum at each portion of the alveolar bone, etc. may be analyzed using the combined three-dimensional image acquired by matching the oral scan image and the CT image. A procedure plan suitable for the patient may be established on the basis of the information analyzed in this way.

If the combined three-dimensional image is acquired (s10), the fixture corresponding to an implant placement position preset on the basis of the acquired combined three-dimensional image is selected. The surgical guide in which at least one guide hole for guiding drilling of a hole for placing the selected fixture is formed is prepared. Information about the placement of the fixture corresponding to each of the guide holes and information about drilling guidance to the hole are calculated and prepared as procedure report information (s20).

Here, the preset implant placement position refers to a tooth to be extracted for the implant procedure or a tooth which the patient wants for the implant procedure among extracted teeth and can be set to one or more.

At this time, if a type of tooth is calculated according to the implant placement position, a diameter, a length, a cross-sectional shape, etc. of the fixture may be selected in view of a mastication pressure of each tooth, the bone density of the alveolar bone, another implant placement position adjacent to the implant placement position, and so on.

To be specific, referring to FIG. 2, a shape, the bone density, etc. of the alveolar bone 2 around the implant placement position 4 are shown in the combined three-dimensional image 1. Further, lower nerve tissues of the alveolar bone 2, arrangement of neighboring teeth 3, etc. may be shown.

At this time, for a stable placement of the fixture, a safety distance of about 1.5 to 2 mm is required around the hole 6 in which the fixture is to be placed. A position and a direction of the hole 6 may be set in view of the safety distance, nerve tissue 5, a position of another hole to be formed adjacent to the hole 6, a position/direction of the crown supported by the fixture, and so on.

If the fixture is selected, the surgical guide is prepared. At this point, it is preferably understood that the preparation of the surgical guide means that design information for manufacturing the surgical guide is acquired or that the acquired design information is input to a manufacturing system to manufacture the actual surgical guide.

Here, a fixing recess that is form-fitted to a profile of the inside of the oral cavity of the patient is formed in one surface of the surgical guide. The surgical guide can be stably fixed to the inside of the oral cavity of the patient by the fixing recess.

With the surgical guide fixed, the guide hole is formed in a portion corresponding to the implant placement position, and a post-implant procedure for drilling a hole in the alveolar bone using the guide hole or inserting the fixture into the hole may be performed.

At this point, referring to FIG. 3, a direction of the guide hole 8 may be set to a hole forming direction 6a or a fixture placing direction. If the direction of the guide hole 8 is set and a diameter of the guide hole 8 is set according to a diameter of the fixture, the design information for the surgical guide may be acquired, and a virtual image 7 of the surgical guide may be shown in the three-dimensional image 1.

Here, a front arrow indicated in FIG. 3 refers to a direction in which the surgical guide is mounted in the oral cavity. The surgical guide may be pushed to a front (or foretooth) lower side in the direction of the arrow with the surgical guide inserted in the oral cavity, so that it can be mounted on the teeth or the gum. A sleeve that substantially and rotatably supports an outer circumference of a drill bit and guides a coupling angle of the fixture or the abutment may be inserted into the guide hole.

Further, a thickness of the surgical guide may be set to a value used when a drill bit insertion depth is corrected with a reference unit length, such that a thickness from a surface of the guide hole to a contact portion between the fixing recess and the inside of the oral cavity corresponds to a distance from the contact portion to a lower end of the drilled hole. Here, it is preferably understood that the contact portion refers to an outer surface of the gum or outer surfaces of remaining teeth of the patient.

At this point, it is preferably understood that the reference unit length refers to a length from a stopper line formed on an outer circumference of a drill to an end of the drill bit. That is, the stopper line may be provided in multiple phases so as to be able to recognize a depth at which the end of the drill bit is inserted from the surface of the guide hole or an upper end of the sleeve past the inside of the guide hole into the tissue of, for instance, the alveolar bone or the gum of the patient.

For example, the length from the stopper line to the end of the drill bit may be 10 mm, 11 mm, 12 mm, or the like. The reference unit length becomes 1 mm. At this point, the distance from the contact portion to the lower end of the drilled hole may have a precise unit valve equal to or less than 1 mm due to a characteristic of living body tissue.

Therefore, as the thickness of the surgical guide is adjusted corresponding to the distance from the contact portion to the lower end of the drilled hole, the distance from the surface of the guide hole or the upper end of the sleeve to the lower end of the drilled hole can be adjusted on the basis of the reference unit length. That is, when the distance from the contact portion to the lower end of the drilled hole is 8.5 mm, the thickness of the surgical guide may be 5.5 mm, 6.5 mm, etc., such that a distance unit from the surface of the guide hole or the upper end of the sleeve to the lower end of the drilled hole becomes 1 mm which is the reference unit length.

In this way, since the drill bit insertion depth using the stopper line can be accurately adjusted on the basis of the surface of the guide hole or the upper end of the sleeve, the drilled hole can be formed with a more accurate depth. At this point, when the position and direction of the guide hole, the shape of the fixing recess, the thickness of the surgical guide, etc. are set corresponding to the implant placement position, a three-dimensional shape of the surgical guide can be acquired with the design information.

When the surgical guide is prepared, the information about the placement of the fixture corresponding to the guide hole and the information about the drilling guidance to the hole are calculated and prepared as the procedure report information. Here, the information about the placement of the fixture preferably includes standardized information including the length, the diameter, and the cross-sectional shape of the fixture, an offset distance from the upper end of the sleeve to the surface of the guide hole, and the drill bit insertion depth from the upper end of the sleeve to the lower end of the fixture.

At this point, the sleeve may be inserted, such that the upper end of the sleeve coincides with the surface of the guide hole according to the implant placement position and that the upper end of the sleeve protrudes from the surface of the guide hole at a predetermined distance. For example, when the offset distance is zero (0), the sleeve is inserted, such that the upper end of the sleeve coincides with the surface of the guide hole. When the offset distance is 1 mm, the sleeve is inserted, such that the upper end of the sleeve protrudes 1 mm from the surface of the guide hole.

The drill bit insertion depth refers to a distance from the upper end of the sleeve into the gum or the alveolar bone of the patient via the inside of the guide hole, into which the drill bit is inserted.

Further, the information about the drilling guidance to the hole preferably includes information about a plurality of drills and information about insertion depth of each of the drill bits. Here, the plurality of drills may be used in a process of forming one hole, and each of the drill bits may be inserted to a different insertion depth.

For example, the process of drilling the hole may include a process of removing the gum, a process of flattening the alveolar bone, a process of forming a point hole, a process of forming an initial hole, a process of expanding the initial hole, a process of adjusting the expanded hole, a process of forming threads, and so on.

To be specific, in the process of removing the gum, a tissue punch is used, and an insertion depth thereof may be set according to a thickness of the gum. In the process of flattening the alveolar bone, a bone flattening drill is used, and an insertion depth thereof may be set according to a height of an exposed surface of the alveolar bone.

Further, in the process of forming the point hole, a guide drill is used. In the process of forming the initial hole, an initial drill is used. In the process of expanding the initial hole, final drills having different diameters are used. In the process of adjusting the expanded hole, a profile drill is used. In the process of forming the threads, a tap drill is used.

At this point, each of the drills may have a different insertion depth. Needless to say, the drills may further include a profile drill that opens an upper portion of the fixture covered by the gum when the abutment is coupled to the placed fixture after the hole is formed. Here, the information about the drilling guidance preferably includes the order of use of each of the drills corresponding to the process order.

Meanwhile, a step of calculating the information about the drilling guidance includes a step of calculating the drill bit insertion depth in each of the processes and a step of setting the drill bit insertion depth in each of the processes.

At this point, the drill bit insertion depth in each of the processes is calculated corresponding to a length from the surface of the surgical guide to the lower end of the drilled hole when the number of processes for the drilled hole is calculated corresponding the diameter of the fixture. Further, the drill bit insertion depth in each of the processes is set on the basis of the number of processes and the plurality of drills selected from a drill database. Here, it is preferably understood that the surface of the surgical guide refers to the upper end of the sleeve fitted into the guide hole.

To be specific, when the fixture is selected, a diameter of the drilled hole suitable for the fixture may be calculated. When the diameter of the drilled hole is calculated, the number of processes for forming the hole may be calculated.

At this point, the process of drilling the hole may include the process of removing the gum, the process of flattening the alveolar bone, the process of forming the point hole, the process of forming the initial hole, the process of expanding the initial hole, the process of adjusting the expanded hole, the process of forming the threads, and so on. Among these processes, the process of expanding the initial hole may be performed a plurality of times depending on the diameter of the drilled hole.

For example, when the diameter of the drilled hole is 4 mm, the process of forming the point hole and the process of forming the initial hole are performed using a guide drill having a diameter of 2 mm and an initial drill having a diameter of 2 mm. The process of expanding the initial hole is repeated three times, and final drills having diameters of 2.7 mm, 3.0 mm, and 3.2 mm are sequentially used. The number of processes suitable for the diameter of each of the drilled holes may be provided in the form of a table. If the diameter of the drilled hole is set, it may be retrieved from the table, and the adequate number of processes may be calculated.

Of course, the calculated number of processes may be separately examined on the basis of the combined three-dimensional image by a group of experts such as a dental technician, a dentist, etc., so that the group of experts can check whether or not the calculated number of processes is suitable for the patient.

At this point, the number of processes may be corrected according to the density of the alveolar bone corresponding to a contact portion of each of the drill bits. To be specific, the density of the alveolar bone may be calculated according to a contrast indicated in the combined three-dimensional image. That is, a bright portion may indicate hard and dense tissue, and a dark portion may indicate soft and loose tissue.

At this point, when the number of processes and the drill for each of the processes are calculated according to the diameter of the fixture, the contact portion of each of the drill bits may be calculated on the basis of the combined three-dimensional image.

When the contact portion of each of the drill bits is calculated, the number of processes may be corrected by omitting or adding the use of the drill depending on the density of the alveolar bone corresponding to the contact portion.

At this point, the calculation of the contact portion may be performed by disposing each of the drills within the combined three-dimensional image according to three-dimensional coordinates of the drilled hole and calculating a duplicate portion between the drill and the alveolar bone, and be automatically performed by manual work of an expert or an image processing program.

Whether or not each of the drills is used according to the density of the alveolar bone is provided in the form of a table, and the table is compared with the density of the alveolar bone corresponding to the contact portion. Thereby, the calculated number of processes can be corrected.

Further, when the length of the fixture is calculated and when the placed depth of the fixture is set, a drill bit insertion depth from the surface of the surgical guide to the lower end of the fixture with the surgical guide fixed to the inside of the oral cavity of the patient may be calculated. For example, if the length of the fixture is 11.5 mm and if a length from the surface of the surgical guide to an upper end of the fixture is 9 mm, the drill bit insertion depth of 20.5 mm may be calculated.

At this point, when the drill bit insertion depth is calculated, the drill bit insertion depth suitable for each of the processes may be calculated. That is, in the process of removing the gum and the process of flattening the alveolar bone, the drill bit insertion depth may be calculated according to a depth from the surface of the surgical guide to the surface of the alveolar bone. In the process of forming the point hole, the drill bit insertion depth may be calculated according to a rate that is set for the calculated drill bit insertion depth.

For example, if the drill bit insertion depth is 20.5 mm, the drill bit insertion depth in the process of forming the point hole may be calculated to be 14.5 mm with a predetermined rate taken into account. At this point, the drill database includes information about lengths and diameters of drill bits of various drills, and contour images of the drill bits of the drills.

A plurality of drills having diameters and lengths of adequate drill bits may be selected according to the number of processes and the drill bit insertion depth for each of the processes, and information about the drill bit insertion depth may be provided for each of the selected drills.

Of course, the step of selecting the drills to provide the information about the drill bit insertion depth for each of the selected drills may be performed by manual work of an expert group. Appropriate drills may be provided in the form of a table according to the number of processes, the diameter and depth of the drilled hole, and the thickness of the surgical guide, and the drill suitable for input numerical values may be automatically selected.

In this way, the number of processes and the drill bit insertion depth for each of the processes, which are suitable for drilling the hole corresponding to each of the guide holes, may be rapidly calculated by several criteria including the size of the fixture, the thickness of the surgical guide, and so on, and the procedure report may be more accurately provided on the basis thereof.

Referring to FIGS. 4 and 5, when the information about the procedure report is prepared (s20), the procedure report is output that includes a summary report 10 in which the information about the procedure report is indicated according to the image of the surgical guide and a protocol report 20 in which the information about the procedure report is filtered and indicated to be matched with each of the guide holes (s30).

To be specific, the information about the procedure report is indicated in the summary report 10 according to a planar image 11 of the surgical guide in which each of the guide holes 12 of the surgical guide can be easily recognized.

At this point, the information about the procedure report which is indicated in the summary report 10 may be preferably provided with the size of the fixture, the offset distance, and the drill bit insertion depth that constitute information about the placement of the fixture. The size of the fixture, the offset distance, and the drill bit insertion depth are preferably classified according to the position of each of the guide holes and are indicated by each of tag images 13.

Here, the plurality of tag images 13 are provided to be classified for each of the guide holes 12 and may be disposed along a contour of the planar image 11 of the surgical guide corresponding to an arrangement of the guide holes 12.

At this point, each of the tag images 13 may be provided as a text image indicating the size 13a of the fixture, the offset distance 13b, and the drill bit insertion depth 13c which correspond to each of the guide holes and be connected to each of the corresponding guide holes by each of leader lines 13g.

In this way, as the plurality of tag images are indicated on the basis of the image of the surgical guide, the summary report 10 is provided to recognize overall information required for the implant procedure, such as the size of the fixture, the disposition of the sleeve, the drill bit insertion depth, etc. with a single glance. As a result, it is possible to accurately drill the hole corresponding to the position of the implant and to easily select and place the appropriate fixture and thus accuracy and convenience of the implant procedure can be improved.

Further, identification numbers 13d of the teeth replaced by the fixtures and sequence images 13f that indicate the order of placing the placement objects are preferably included in the summary report 10. For example, the identification numbers 13d of the teeth may be sequentially set from the middle to the inside in such a manner that 11 is given to a left front tooth and 18 is given to a left molar and that 21 is given to a right front tooth and 28 is given to a right molar.

Therefore, since the tooth of the patient which correspond to each of the guide holes can be easily recognized, the surgical guide can be easily mounted at an accurate position in the oral cavity of the patient. Here, the placement object preferably includes the fixture, the abutment coupled to the fixture, and a guide fix for fixing the surgical guide.

To be specific, in the case of edentulous jaws for which no remaining teeth are present in the oral cavity of the patient, a pin-shaped fixing means called a guide fix may be placed before the fixture is placed. At this point, the guide fix is placed by forming a hole having a narrower depth and a smaller diameter than the drilled hole for placing the fixture.

The guide fixes may be placed in the alveolar bone of the patient using some guide holes that are disposed to form a triangular or quadrilateral shape among the guide holes of the surgical guide and fix the surgical guide. When the surgical guide is fixed by the guide fixes, the holes matched with the fixtures are drilled along the guide holes other than the guide holes in which the guide fixes are placed, and the fixtures are placed.

After the surgical guide is fixed using the placed fixtures, the guide fixes are removed, the holes suitable for the fixtures to be placed in the corresponding guide holes are drilled, and then the fixtures are placed. Thus, the guide fixes and the fixtures can be placed in the right order. At this point, preferably, each of the tag images 13 further includes a placement object image 13e of each of the placement objects such as the abutment and guide fix that are placed in the guide holes. The surgeon can more easily recognize the order of the placement of the guide fixes and the placement object placed in each of the guide holes from the sequence images 13f and the placement object images 13e.

Further, the information about the procedure report is filtered and indicated in each of the protocol reports 20 so as to be matched to one of the guide holes. That is, the plurality of protocol reports 20 are provided to correspond to the number of guide holes. Each of the protocol reports 20 is provided for each of the guide holes 12. The information about the procedure report matched to one of the guide holes can be filtered and indicated in each of the protocol reports 20.

The plurality of protocol reports may naturally be provided for each of the guide holes. However, after images of the representative drills are arranged at an upper portion of the protocol report, the guide holes and whether or not each of the guide holes is used may be indicated at a lower portion of the protocol report in the list. That is, each row of the list in which whether or not each of the guide holes is used is shown indicates each of the guide holes, and whether or not each of the guide holes is used is shown according to each of the rows. At this point, the information about the procedure report matched to one of the guide holes may be filtered and indicated in each of the rows.

Here, preferably, the information about each of the drills is converted to an image according to the information about the insertion depth, and the converted images are arranged and indicated in the protocol report 20 in temporal order according to the preset order of the processes.

To be specific, in the protocol report 20, thicknesses of the gum 23 and the alveolar bone 24 at a portion corresponding to the guide hole may be converted to and indicated as images, and an image 22 of the sleeve provided for the guide hole may be indicated according to the offset distance.

The plurality of pieces of information about the drills used in the process of drilling the hole are converted and indicated as images, and the images 21 of the drills may be disposed in a positional relationship with the images of the gum 23 and the alveolar bone 24 according to the drill bit insertion depth for each of the processes. At this point, the images 21 of the drills may be arranged to be matched with the order of the processes in temporal order. For example, the images of the drills used in the earlier processes may be indicated toward the left side, and the images of the drills used in the later processes may be indicated toward the right side.

Therefore, unlike using the process-specific drills selected depending on the experience and memory of the surgeon to match with the processes, types of the drills used in each of the processes during the procedure and the order of the use of the drills can be easily recognized using the images of the arranged drills, so that the convenience of the procedure can be improved. Moreover, since the procedure can be performed while the types of the drills used in each of the processes during the procedure and the order of the use of the drills are checked, mistakes and confusion of the surgeon are minimized, so that the accuracy of the procedure can be improved. At this point, the procedure report may be output to a computerized file or a printed matter.

Meanwhile, if the procedure report is output (s30), the output procedure report is delivered according to information about delivery of the surgical guide (s40).

Here, the information about the delivery of the surgical guide includes information about an address, an e-mail, or an identification (ID) of a requestor. The procedure report output to the printed matter may be delivered with the manufactured surgical guide by post, and the procedure report output to the computerized file may also be delivered over a telecommunication network.

In this way, the procedure report in which the information about the drills used in the process of drilling the hole and the information about the fixture placed in each of the drilled holes are indicated is provided along with the surgical guide that guides the drilling of the hole for placing the fixture. Accordingly, all instruments used for the implant procedure can be easily recognized, so that the convenience of the procedure can be improved.

Meanwhile, referring to FIGS. 5 and 6, an index of the alveolar bone in which the densities of the alveolar bone at the portions corresponding to the guide holes are classified according to a preset range of a plurality of densities is indicated in the protocol report 20, and the pieces of information about the drills are preferably listed and indicated according to suggested drilling steps corresponding to the index of the alveolar bone.

To be specific, the densities of the alveolar bone may be indicated in the combined three-dimensional image as a contrast and be classified on the basis of the contrast. At this time, the range of the densities may be classified into soft, medium, and hard. The soft classification refers to a very dark portion when the alveolar bone is indicated, and the hard refers to a very bright portion when the alveolar bone is indicated. Here, the range of the densities may be set to different ranges according to the drill and strength of the fixture.

At this point, portions of the alveolar bone may be classified according to the range of the densities and be indicated in the combined three-dimensional image in color. The color-specific classification of the portions of the alveolar bone may be automatically processed according to the input contrast using an image processing program, and be manually processed by an expert including a dental technician and a dentist. For example, the hardest portion may be indicated by a yellow D4 and a green D3, a medium hardness portion may be indicated by a blue D2, and a soft portion may be indicated by a grey D1. At this point, FIG. 6 illustrates the alveolar bone of the combined three-dimensional image at the portion corresponding to one of the guide holes, when cut in a direction perpendicular to a direction in which the hole is drilled.

In this way, since the portions of the alveolar bone indicated in the combined three-dimensional image is classified according to the set range and are indicated in color, the densities of the alveolar bone at the portion at which each of the drills is brought into contact with the alveolar bone can be easily recognized. At this point, the alveolar bone index 25 may be indicated below of each of the drills 21 in the protocol report, and the densities of the alveolar bone at the portion at which each of the drills is brought into contact with the alveolar bone may be recognized from the alveolar bone index 25.

The suggested drilling steps corresponding to the classified range of the densities may be indicated in the protocol report in the form of a list. That is, the list may indicate a drilling step when the alveolar bone is soft, a drilling step when the alveolar bone is medium, and a drilling step when the alveolar bone is hard. For example, when the alveolar bone is soft, the process of expanding the initial hole using the final drill may be performed, the expanded hole may be adjusted to the abutment profile, and the fixture may be immediately placed.

Thus, the surgeon can easily recognize the densities of the alveolar bone at the portion at which each of the drills is brought into contact with the alveolar bone from the alveolar bone index 25. A criterion for adding a necessary drilling process or omitting an unnecessary drilling process can be established by the list, so that the procedure can be performed in a more efficient and accurate way.

With the aforementioned configuration, the method for providing the procedure guide information using the surgical guide for the dental implant according to the embodiment of the present invention provides the follow effects.

First, since the procedure report in which the information about the drills used in the process of drilling the hole and the information about the fixture placed in each of the drilled holes are indicated by the images is provided along with the surgical guide that guides the drilling of the hole for placing the fixture, the convenience of the implant procedure can be improved.

Second, since the summary report is provided, such that, due to the plurality of tag images being indicated on the basis of the image of the surgical guide, because all the pieces of information required for the implant procedure including the size of the fixture, the disposition of the sleeve, the drill bit insertion depth, etc. are recognized with a single glance, the accuracy of the implant procedure can be improved by accurately drilling the hole corresponding to the implant placement position and providing the accurate information about the fixture suitable for the drilling.

Third, since the pieces of information about the drills are converted to the images, are arranged according to the order of the processes, and are indicated in the protocol report, the types of the drills used in each of the processes during the procedure and the order of the use of the drills can be easily recognized, so that mistakes and confusion by the surgeon are minimized.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A method for providing procedure guide information using a surgical guide for a dental implant, the method comprising:
    a first step of causing a computed tomography (CT) image and an oral scan image of an inside of an oral cavity of a patient to be image-matched to acquire a combined three-dimensional image;
    a second step of selecting a fixture corresponding to a preset implant placement position on the basis of the acquired combined three-dimensional image, preparing the surgical guide in which at least one guide hole configured to guide drilling of a hole used to place the fixture is formed, and causing information about the placement of the fixture corresponding to the guide hole and information about drilling guidance to the hole to be calculated and prepared as information about a procedure report;
    a third step of outputting the procedure report in which a summary report in which the information about the procedure report is indicated along an image of the surgical guide and a protocol report in which the information about the procedure report is filtered and indicated to be matched to one of the guide holes are included; and a fourth step of delivering the output procedure report according to information about delivery of the surgical guide, wherein the second step further includes:

calculating the number of processes in correspondence with a diameter of the fixture and a drill bit insertion depth for each of the processes in correspondence with a length from a surface of the surgical guide to a lower end of the fixture; and selecting a plurality of drills from a database for the drills in correspondence to the number of processes and the drill bit insertion depth for each of the processes, and setting information about the insertion depth for each of the drills.

2. The method of claim 1, wherein:

the information about the placement of the fixture includes a size of the fixture, an offset distance from an upper end of a sleeve inserted into the guide hole to a surface of the guide hole, and a drill bit insertion depth from the upper end of the sleeve to a lower end of the fixture; and the information about the placement of the fixture is indicated in the summary report in the third step as each of tag images classified according to the position corresponding to the guide hole.

3. The method of claim 1, wherein:

the information about the drilling guidance to the hole includes information about a plurality of drills and information about an insertion depth for each of the drills; and the information about the drills is converted to images according to the information about the insertion depth in the protocol report in the third step, and the converted images are arranged and indicated in temporal order according to a preset order of the processes.

4. The method of claim 3, wherein:

an index of an alveolar bone in which densities of the alveolar bone at a portion corresponding to the guide hole are classified according to a preset range of a plurality of densities in the protocol report in the third step; and the information about the drills is indicated in a list according to a suggested drilling step corresponding to the index of the alveolar bone.

* * * * *